(12) United States Patent
McKenna et al.

(10) Patent No.: US 8,469,956 B2
(45) Date of Patent: Jun. 25, 2013

(54) VARIABLE RESISTOR JAW

(75) Inventors: Nicole McKenna, Boulder, CO (US);
Robert H. Wham, Boulder, CO (US)

(73) Assignee: Covidien LP, Mansfield, MA (US)

( * ) Notice: Subject to any disclaimer, the term of this patent is extended or adjusted under 35 U.S.C. 154(b) by 917 days.

(21) Appl. No.: 12/176,679

(22) Filed: Jul. 21, 2008

(65) Prior Publication Data

US 2010/0016857 A1 Jan. 21, 2010

(51) Int. Cl.
*A61B 18/14* (2006.01)

(52) U.S. Cl.
USPC ............................................. 606/51; 606/52

(58) Field of Classification Search
USPC ........................... 606/38, 48, 50–52; 600/393
See application file for complete search history.

(56) References Cited

U.S. PATENT DOCUMENTS

| | | |
|---|---|---|
| 371,664 A | 10/1887 | Brannan et al. |
| 702,472 A | 6/1902 | Pignolet |
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |

(Continued)

FOREIGN PATENT DOCUMENTS

| | | |
|---|---|---|
| CA | 2104423 | 2/1994 |
| DE | 2415263 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Michael Peffley
*Assistant Examiner* — Thomas Giuliani (57) ABSTRACT

A bipolar forceps for sealing tissue includes an end effector assembly having opposing first and second jaw members each having a proximal end and a distal end. A first electrically conductive surface having two or more conductive sealing plates and a dielectric layer is operably coupled to the first jaw member. Each sealing plate is connected to a reactive element and positioned along the first electrically conductive surface from the proximal end to the distal end. The reactive elements of the sealing plates have different impedances. A second electrically conductive surface having at least one conductive sealing plate is operably coupled to the second jaw member. Each electrically conductive surface on the jaw members connects to a source of electrosurgical energy such that the sealing plates are capable of conducting energy through tissue held therebetween to effect a tissue seal.

13 Claims, 6 Drawing Sheets

U.S. PATENT DOCUMENTS

| | | |
|---|---|---|
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |

| | | | | | |
|---|---|---|---|---|---|
| 5,422,567 A | 6/1995 | Matsunaga | 5,620,453 A | 4/1997 | Nallakrishnan |
| 5,423,810 A | 6/1995 | Goble et al. | 5,620,459 A | 4/1997 | Lichtman |
| 5,425,690 A | 6/1995 | Chang | 5,624,452 A | 4/1997 | Yates |
| 5,425,739 A | 6/1995 | Jessen | 5,626,578 A | 5/1997 | Tihon |
| 5,429,616 A | 7/1995 | Schaffer | 5,626,609 A | 5/1997 | Zvenyatsky et al. |
| 5,431,672 A | 7/1995 | Cote et al. | 5,630,833 A | 5/1997 | Katsaros et al. |
| 5,431,674 A | 7/1995 | Basile et al. | 5,637,110 A | 6/1997 | Pennybacker et al. |
| 5,437,292 A | 8/1995 | Kipshidze et al. | 5,638,003 A | 6/1997 | Hall |
| 5,438,302 A | 8/1995 | Goble | 5,643,294 A | 7/1997 | Tovey et al. |
| 5,439,478 A | 8/1995 | Palmer | 5,647,869 A | 7/1997 | Goble et al. |
| 5,441,517 A | 8/1995 | Kensey et al. | 5,647,871 A | 7/1997 | Levine et al. |
| 5,443,463 A | 8/1995 | Stern et al. | 5,649,959 A | 7/1997 | Hannam et al. |
| 5,443,464 A | 8/1995 | Russell et al. | 5,655,650 A | 8/1997 | Naitou |
| 5,443,480 A | 8/1995 | Jacobs et al. | 5,658,281 A | 8/1997 | Heard |
| 5,445,638 A | 8/1995 | Rydell et al. | D384,413 S | 9/1997 | Zlock et al. |
| 5,445,658 A | 8/1995 | Durrfeld et al. | 5,662,667 A | 9/1997 | Knodel |
| 5,449,480 A | 9/1995 | Kuriya et al. | 5,665,100 A | 9/1997 | Yoon |
| 5,451,224 A | 9/1995 | Goble et al. | 5,667,526 A | 9/1997 | Levin |
| 5,454,823 A | 10/1995 | Richardson et al. | 5,674,220 A | 10/1997 | Fox et al. |
| 5,454,827 A | 10/1995 | Aust et al. | 5,674,229 A | 10/1997 | Tovey et al. |
| 5,456,684 A | 10/1995 | Schmidt et al. | 5,681,282 A | 10/1997 | Eggers et al. |
| 5,458,598 A | 10/1995 | Feinberg et al. | 5,688,270 A | 11/1997 | Yates et al. |
| 5,460,629 A | 10/1995 | Shlain et al. | 5,690,652 A | 11/1997 | Wurster et al. |
| 5,461,765 A | 10/1995 | Linden et al. | 5,690,653 A | 11/1997 | Richardson et al. |
| 5,462,546 A | 10/1995 | Rydell | 5,693,051 A | 12/1997 | Schulze et al. |
| 5,472,442 A | 12/1995 | Klicek | 5,693,920 A | 12/1997 | Maeda |
| 5,472,443 A | 12/1995 | Cordis et al. | 5,695,522 A | 12/1997 | LeMaire, III et al. |
| 5,478,351 A | 12/1995 | Meade et al. | 5,700,261 A | 12/1997 | Brinkerhoff |
| 5,480,406 A | 1/1996 | Nolan et al. | 5,700,270 A | 12/1997 | Peyser et al. |
| 5,480,409 A | 1/1996 | Riza | 5,702,390 A | 12/1997 | Austin et al. |
| 5,484,436 A | 1/1996 | Eggers et al. | 5,707,369 A | 1/1998 | Vaitekunas et al. |
| 5,496,312 A | 3/1996 | Klicek | 5,709,680 A | 1/1998 | Yates et al. |
| 5,496,317 A | 3/1996 | Goble et al. | 5,716,366 A | 2/1998 | Yates |
| 5,496,347 A | 3/1996 | Hashiguchi et al. | 5,720,744 A | 2/1998 | Eggleston et al. |
| 5,499,997 A | 3/1996 | Sharpe et al. | 5,722,421 A | 3/1998 | Francese et al. |
| 5,509,922 A | 4/1996 | Aranyi et al. | 5,725,536 A | 3/1998 | Oberlin et al. |
| 5,512,721 A | 4/1996 | Young et al. | 5,727,428 A | 3/1998 | LeMaire, III et al. |
| 5,514,134 A | 5/1996 | Rydell et al. | 5,735,848 A | 4/1998 | Yates et al. |
| 5,527,313 A | 6/1996 | Scott et al. | 5,743,906 A | 4/1998 | Parins et al. |
| 5,528,833 A | 6/1996 | Sakuma | 5,752,973 A | 5/1998 | Kieturakis |
| 5,529,067 A | 6/1996 | Larsen et al. | 5,755,717 A | 5/1998 | Yates et al. |
| 5,531,744 A | 7/1996 | Nardella et al. | 5,759,188 A | 6/1998 | Yoon |
| 5,536,251 A | 7/1996 | Evard et al. | 5,766,130 A | 6/1998 | Selmonosky |
| 5,540,684 A | 7/1996 | Hassler, Jr. | 5,766,166 A | 6/1998 | Hooven |
| 5,540,685 A | 7/1996 | Parins et al. | 5,766,170 A | 6/1998 | Eggers |
| 5,540,706 A | 7/1996 | Aust et al. | 5,766,196 A | 6/1998 | Griffiths |
| 5,540,715 A | 7/1996 | Katsaros et al. | 5,769,849 A | 6/1998 | Eggers |
| 5,542,945 A | 8/1996 | Fritzsch | 5,772,655 A | 6/1998 | Bauer et al. |
| 5,558,671 A | 9/1996 | Yates | 5,772,670 A | 6/1998 | Brosa |
| 5,558,672 A | 9/1996 | Edwardds et al. | 5,776,128 A | 7/1998 | Eggers |
| 5,562,619 A | 10/1996 | Mirarchi et al. | 5,776,130 A | 7/1998 | Buysse et al. |
| 5,562,699 A | 10/1996 | Heimberger et al. | 5,779,646 A | 7/1998 | Koblish et al. |
| 5,562,720 A | 10/1996 | Stern et al. | 5,779,701 A | 7/1998 | McBrayer et al. |
| 5,564,615 A | 10/1996 | Bishop et al. | H1745 H | 8/1998 | Paraschac |
| 5,569,241 A | 10/1996 | Edwards | 5,792,137 A | 8/1998 | Carr et al. |
| 5,569,243 A | 10/1996 | Kortenbach et al. | 5,792,165 A | 8/1998 | Klieman et al. |
| 5,571,100 A | 11/1996 | Goble et al. | 5,792,177 A | 8/1998 | Kaseda |
| 5,573,424 A | 11/1996 | Poppe | 5,797,537 A | 8/1998 | Oberlin et al. |
| 5,573,534 A | 11/1996 | Stone | 5,797,927 A | 8/1998 | Yoon |
| 5,573,535 A | 11/1996 | Viklund | 5,797,938 A | 8/1998 | Paraschac et al. |
| 5,575,799 A | 11/1996 | Bolanos et al. | 5,797,941 A | 8/1998 | Schulze et al. |
| 5,575,805 A | 11/1996 | Li | 5,797,958 A | 8/1998 | Yoon |
| 5,578,052 A | 11/1996 | Koros et al. | 5,800,449 A | 9/1998 | Wales |
| 5,579,781 A | 12/1996 | Cooke | 5,807,393 A | 9/1998 | Williamson, IV et al. |
| 5,582,611 A | 12/1996 | Tsukagoshi et al. | 5,810,764 A | 9/1998 | Eggers et al. |
| 5,582,617 A | 12/1996 | Klieman et al. | 5,810,805 A | 9/1998 | Sutcu et al. |
| 5,585,896 A | 12/1996 | Yamazaki et al. | 5,810,808 A | 9/1998 | Eggers |
| 5,590,570 A | 1/1997 | LeMaire, III et al. | 5,810,811 A * | 9/1998 | Yates et al. ............ 606/50 |
| 5,591,181 A | 1/1997 | Stone et al. | 5,810,877 A | 9/1998 | Roth et al. |
| 5,597,107 A | 1/1997 | Knodel et al. | 5,814,043 A | 9/1998 | Shapeton |
| 5,601,224 A | 2/1997 | Bishop et al. | 5,814,054 A | 9/1998 | Kortenbach et al. |
| 5,601,601 A | 2/1997 | Tal et al. | 5,817,083 A | 10/1998 | Shemesh et al. |
| 5,601,641 A | 2/1997 | Stephens | 5,817,119 A | 10/1998 | Klieman et al. |
| 5,603,711 A | 2/1997 | Parins et al. | 5,820,630 A | 10/1998 | Lind |
| 5,603,723 A | 2/1997 | Aranyi et al. | 5,824,978 A | 10/1998 | Karasik et al. |
| 5,611,798 A | 3/1997 | Eggers | 5,827,271 A | 10/1998 | Buysse et al. |
| 5,611,808 A | 3/1997 | Hossain et al. | 5,827,279 A | 10/1998 | Hughett et al. |
| 5,611,813 A | 3/1997 | Lichtman | 5,827,281 A | 10/1998 | Levin |
| 5,620,415 A | 4/1997 | Lucey et al. | 5,827,323 A | 10/1998 | Klieman et al. |

| Patent | Kind | Date | Inventor |
|---|---|---|---|
| 5,827,548 | A | 10/1998 | Lavallee et al. |
| 5,833,690 | A | 11/1998 | Yates et al. |
| 5,843,080 | A | 12/1998 | Fleenor et al. |
| 5,849,022 | A | 12/1998 | Sakashita et al. |
| 5,853,412 | A | 12/1998 | Mayenberger |
| 5,859,527 | A | 1/1999 | Cook |
| 5,860,976 | A | 1/1999 | Billings et al. |
| 5,876,401 | A | 3/1999 | Schulze et al. |
| 5,876,412 | A | 3/1999 | Piraka |
| 5,882,567 | A | 3/1999 | Cavallaro et al. |
| 5,891,141 | A | 4/1999 | Rydell |
| 5,891,142 | A | 4/1999 | Eggers et al. |
| 5,893,863 | A | 4/1999 | Yoon |
| 5,893,875 | A | 4/1999 | O'Connor et al. |
| 5,893,877 | A | 4/1999 | Gampp, Jr. et al. |
| 5,897,563 | A | 4/1999 | Yoon et al. |
| 5,902,301 | A | 5/1999 | Olig |
| 5,906,630 | A | 5/1999 | Anderhub et al. |
| 5,908,420 | A | 6/1999 | Parins et al. |
| 5,908,432 | A | 6/1999 | Pan |
| 5,911,719 | A | 6/1999 | Eggers |
| 5,913,874 | A | 6/1999 | Berns et al. |
| 5,921,916 | A | 7/1999 | Aeikens et al. |
| 5,921,984 | A | 7/1999 | Sutcu et al. |
| 5,925,043 | A | 7/1999 | Kumar et al. |
| 5,928,136 | A | 7/1999 | Barry |
| 5,935,126 | A | 8/1999 | Riza |
| 5,941,869 | A | 8/1999 | Patterson et al. |
| 5,944,718 | A | 8/1999 | Dafforn et al. |
| 5,951,546 | A | 9/1999 | Lorentzen |
| 5,951,549 | A | 9/1999 | Richardson et al. |
| 5,954,720 | A | 9/1999 | Wilson et al. |
| 5,954,731 | A | 9/1999 | Yoon |
| 5,954,733 | A | 9/1999 | Yoon |
| 5,957,923 | A | 9/1999 | Hahnen et al. |
| 5,957,937 | A | 9/1999 | Yoon |
| 5,960,544 | A | 10/1999 | Beyers |
| 5,961,514 | A | 10/1999 | Long et al. |
| 5,964,758 | A | 10/1999 | Dresden |
| 5,976,132 | A | 11/1999 | Morris |
| 5,984,932 | A | 11/1999 | Yoon |
| 5,984,938 | A | 11/1999 | Yoon |
| 5,984,939 | A | 11/1999 | Yoon |
| 5,989,277 | A | 11/1999 | LeMaire, III et al. |
| 5,993,466 | A | 11/1999 | Yoon |
| 5,993,467 | A | 11/1999 | Yoon |
| 5,997,565 | A | 12/1999 | Inoue |
| 6,004,332 | A | 12/1999 | Yoon et al. |
| 6,004,335 | A | 12/1999 | Vaitekunas et al. |
| 6,010,516 | A | 1/2000 | Hulka et al. |
| 6,017,358 | A | 1/2000 | Yoon et al. |
| 6,021,693 | A | 2/2000 | Feng-Sing |
| 6,024,741 | A | 2/2000 | Williamson et al. |
| 6,024,743 | A | 2/2000 | Edwards |
| 6,024,744 | A | 2/2000 | Kese et al. |
| 6,027,522 | A | 2/2000 | Palmer |
| 6,030,384 | A | 2/2000 | Nezhat |
| 6,033,399 | A | 3/2000 | Gines |
| 6,039,733 | A | 3/2000 | Buysse et al. |
| 6,041,679 | A | 3/2000 | Slater et al. |
| 6,050,996 | A | 4/2000 | Schmaltz et al. |
| 6,053,914 | A | 4/2000 | Eggers et al. |
| 6,053,933 | A | 4/2000 | Balazs et al. |
| D424,694 | S | 5/2000 | Tetzlaff et al. |
| D425,201 | S | 5/2000 | Tetzlaff et al. |
| 6,059,782 | A | 5/2000 | Novak et al. |
| 6,066,139 | A | 5/2000 | Ryan et al. |
| 6,074,386 | A | 6/2000 | Goble et al. |
| 6,077,287 | A | 6/2000 | Taylor et al. |
| 6,080,180 | A | 6/2000 | Yoon et al. |
| RE36,795 | E | 7/2000 | Rydell |
| 6,083,223 | A | 7/2000 | Baker |
| 6,086,586 | A | 7/2000 | Hooven |
| 6,086,601 | A | 7/2000 | Yoon |
| 6,090,107 | A | 7/2000 | Borgmeier et al. |
| 6,096,037 | A | 8/2000 | Mulier et al. |
| 6,099,550 | A | 8/2000 | Yoon |
| 6,102,909 | A | 8/2000 | Chen et al. |
| 6,106,542 | A | 8/2000 | Toybin et al. |
| 6,110,171 | A | 8/2000 | Rydell |
| 6,113,596 | A | 9/2000 | Hooven et al. |
| 6,113,598 | A | 9/2000 | Baker |
| 6,117,158 | A | 9/2000 | Measamer et al. |
| 6,122,549 | A | 9/2000 | Sharkey et al. |
| 6,123,701 | A | 9/2000 | Nezhat |
| H1904 | H | 10/2000 | Yates et al. |
| 6,126,658 | A | 10/2000 | Baker |
| 6,126,665 | A | 10/2000 | Yoon |
| 6,139,563 | A | 10/2000 | Cosgrove, III et al. |
| 6,143,005 | A | 11/2000 | Yoon et al. |
| 6,152,923 | A | 11/2000 | Ryan |
| 6,162,220 | A | 12/2000 | Nezhat |
| 6,171,316 | B1 | 1/2001 | Kovac et al. |
| 6,174,309 | B1 | 1/2001 | Wrublewski et al. |
| 6,178,628 | B1 | 1/2001 | Clemens et al. |
| 6,179,834 | B1 | 1/2001 | Buysse et al. |
| 6,179,837 | B1 | 1/2001 | Hooven |
| 6,183,467 | B1 | 2/2001 | Shapeton et al. |
| 6,187,003 | B1 | 2/2001 | Buysse et al. |
| 6,190,386 | B1 | 2/2001 | Rydell |
| 6,190,400 | B1 | 2/2001 | Vandemoer et al. |
| 6,193,718 | B1 | 2/2001 | Kortenbach et al. |
| 6,206,876 | B1 | 3/2001 | Levine et al. |
| 6,206,877 | B1 | 3/2001 | Kese et al. |
| 6,206,893 | B1 | 3/2001 | Klein et al. |
| 6,214,028 | B1 | 4/2001 | Yoon et al. |
| 6,217,602 | B1 | 4/2001 | Redmon |
| 6,217,615 | B1 | 4/2001 | Sioshansi et al. |
| 6,221,039 | B1 | 4/2001 | Durgin et al. |
| 6,223,100 | B1 | 4/2001 | Green |
| 6,224,593 | B1 | 5/2001 | Ryan et al. |
| 6,224,614 | B1 | 5/2001 | Yoon |
| 6,228,080 | B1 | 5/2001 | Gines |
| 6,228,083 | B1 | 5/2001 | Lands et al. |
| 6,248,124 | B1 | 6/2001 | Pedros et al. |
| 6,248,944 | B1 | 6/2001 | Ito |
| 6,261,307 | B1 | 7/2001 | Yoon et al. |
| 6,267,761 | B1 | 7/2001 | Ryan |
| 6,270,497 | B1 | 8/2001 | Sekino et al. |
| 6,270,508 | B1 | 8/2001 | Klieman et al. |
| 6,273,887 | B1 | 8/2001 | Yamauchi et al. |
| 6,277,117 | B1 | 8/2001 | Tetzlaff et al. |
| 6,280,458 | B1 | 8/2001 | Boche et al. |
| 6,283,961 | B1 | 9/2001 | Underwood et al. |
| D449,886 | S | 10/2001 | Tetzlaff et al. |
| 6,298,550 | B1 | 10/2001 | Kirwan |
| 6,302,424 | B1 | 10/2001 | Gisinger et al. |
| 6,319,262 | B1 | 11/2001 | Bates et al. |
| 6,319,451 | B1 | 11/2001 | Brune |
| 6,322,561 | B1 | 11/2001 | Eggers et al. |
| 6,322,580 | B1 | 11/2001 | Kanner |
| 6,325,795 | B1 | 12/2001 | Lindemann et al. |
| 6,334,860 | B1 | 1/2002 | Dorn |
| 6,334,861 | B1 | 1/2002 | Chandler et al. |
| 6,345,532 | B1 | 2/2002 | Coudray et al. |
| 6,350,264 | B1 | 2/2002 | Hooven |
| 6,352,536 | B1 | 3/2002 | Buysse et al. |
| 6,358,249 | B1 | 3/2002 | Chen et al. |
| 6,358,259 | B1 | 3/2002 | Swain et al. |
| 6,358,268 | B1 | 3/2002 | Hunt et al. |
| 6,364,879 | B1 | 4/2002 | Chen et al. |
| D457,958 | S | 5/2002 | Dycus et al. |
| D457,959 | S | 5/2002 | Tetzlaff et al. |
| 6,387,094 | B1 | 5/2002 | Eitenmuller |
| 6,391,035 | B1 | 5/2002 | Appleby et al. |
| 6,398,779 | B1 | 6/2002 | Buysse et al. |
| 6,402,747 | B1 | 6/2002 | Lindemann et al. |
| 6,409,728 | B1 | 6/2002 | Ehr et al. |
| H2037 | H | 7/2002 | Yates et al. |
| 6,419,675 | B1 | 7/2002 | Gallo, Sr. |
| 6,425,896 | B1 | 7/2002 | Baltschun et al. |
| 6,432,112 | B2 | 8/2002 | Brock et al. |
| 6,440,144 | B1 | 8/2002 | Bacher |
| 6,443,952 | B1 | 9/2002 | Mulier et al. |
| 6,443,970 | B1 | 9/2002 | Schulze et al. |
| 6,451,018 | B1 | 9/2002 | Lands et al. |
| 6,458,125 | B1 | 10/2002 | Cosmescu |
| 6,458,128 | B1 | 10/2002 | Schulze |

| | | | | | | |
|---|---|---|---|---|---|---|
| 6,458,130 B1 | 10/2002 | Frazier et al. | | 6,802,843 B2 | 10/2004 | Truckai et al. |
| 6,461,352 B2 | 10/2002 | Morgan et al. | | 6,808,525 B2 | 10/2004 | Latterell et al. |
| 6,461,368 B2 | 10/2002 | Fogarty et al. | | D499,181 S | 11/2004 | Dycus et al. |
| 6,464,701 B1 | 10/2002 | Hooven et al. | | 6,818,000 B2 | 11/2004 | Muller et al. |
| 6,464,702 B2 | 10/2002 | Schulze et al. | | 6,821,285 B2 | 11/2004 | Laufer et al. |
| 6,464,704 B2 | 10/2002 | Schmaltz et al. | | 6,835,200 B2 | 12/2004 | Laufer et al. |
| 6,485,489 B2 | 11/2002 | Teirstein et al. | | 6,857,357 B2 | 2/2005 | Fujii |
| 6,494,888 B1 | 12/2002 | Laufer et al. | | 6,860,880 B2 | 3/2005 | Treat et al. |
| 6,500,176 B1 | 12/2002 | Truckai et al. | | 6,887,240 B1 | 5/2005 | Lands et al. |
| 6,506,196 B1 | 1/2003 | Laufer | | 6,889,116 B2 | 5/2005 | Jinno |
| 6,508,815 B1 | 1/2003 | Strul et al. | | 6,914,201 B2 | 7/2005 | Van Vooren et al. |
| 6,511,480 B1 | 1/2003 | Tetzlaff et al. | | 6,926,716 B2 | 8/2005 | Baker et al. |
| 6,514,215 B1 | 2/2003 | Ouchi | | 6,929,644 B2 | 8/2005 | Truckai et al. |
| 6,514,252 B2 | 2/2003 | Nezhat et al. | | 6,932,810 B2 | 8/2005 | Ryan |
| 6,517,539 B1 | 2/2003 | Smith et al. | | 6,932,816 B2 | 8/2005 | Phan |
| 6,527,771 B1 | 3/2003 | Weadock et al. | | 6,934,134 B2 | 8/2005 | Mori et al. |
| 6,533,784 B2 | 3/2003 | Truckai et al. | | 6,936,061 B2 | 8/2005 | Sasaki |
| 6,545,239 B2 | 4/2003 | Spedale et al. | | D509,297 S | 9/2005 | Wells |
| 6,558,385 B1 | 5/2003 | McClurken et al. | | 6,942,662 B2 | 9/2005 | Goble et al. |
| 6,562,037 B2 | 5/2003 | Paton et al. | | 6,943,311 B2 | 9/2005 | Miyako |
| 6,569,105 B1 | 5/2003 | Kortenbach et al. | | 6,953,430 B2 | 10/2005 | Kidooka |
| 6,582,450 B2 | 6/2003 | Ouchi | | 6,953,461 B2 | 10/2005 | McClurken et al. |
| 6,585,735 B1 | 7/2003 | Frazier et al. | | 6,958,070 B2 | 10/2005 | Witt et al. |
| 6,602,252 B2 | 8/2003 | Mollenauer | | 6,960,210 B2 | 11/2005 | Lands et al. |
| 6,605,790 B2 | 8/2003 | Yoshida | | 6,964,662 B2 | 11/2005 | Kidooka |
| 6,616,658 B2 | 9/2003 | Ineson | | 6,966,907 B2 | 11/2005 | Goble |
| 6,616,661 B2 | 9/2003 | Wellman et al. | | 6,972,017 B2 | 12/2005 | Smith et al. |
| 6,620,161 B2 | 9/2003 | Schulze et al. | | 6,977,495 B2 | 12/2005 | Donofrio |
| 6,620,184 B2 | 9/2003 | De Laforcade et al. | | 6,979,786 B2 | 12/2005 | Aukland et al. |
| 6,626,901 B1 | 9/2003 | Treat et al. | | 6,981,628 B2 | 1/2006 | Wales |
| 6,638,287 B2 | 10/2003 | Danitz et al. | | 6,987,244 B2 | 1/2006 | Bauer |
| 6,641,595 B1 | 11/2003 | Moran et al. | | 6,994,707 B2 | 2/2006 | Ellman et al. |
| 6,652,514 B2 | 11/2003 | Ellman et al. | | 6,994,709 B2 | 2/2006 | Iida |
| 6,652,521 B2 | 11/2003 | Schulze | | 6,997,931 B2 | 2/2006 | Sauer et al. |
| 6,656,175 B2 | 12/2003 | Francischelli et al. | | 7,001,381 B2 | 2/2006 | Harano et al. |
| 6,656,177 B2 | 12/2003 | Truckai et al. | | 7,011,657 B2 | 3/2006 | Truckai et al. |
| 6,660,072 B2 | 12/2003 | Chatterjee | | 7,033,354 B2 | 4/2006 | Keppel |
| 6,663,639 B1 | 12/2003 | Laufer et al. | | 7,033,356 B2 | 4/2006 | Latterell et al. |
| 6,663,641 B1 | 12/2003 | Kovac et al. | | 7,041,102 B2 | 5/2006 | Truckai et al. |
| 6,666,854 B1 | 12/2003 | Lange | | 7,044,948 B2 | 5/2006 | Keppel |
| 6,669,696 B2 | 12/2003 | Bacher et al. | | 7,052,489 B2 | 5/2006 | Griego et al. |
| 6,673,092 B1 | 1/2004 | Bacher | | 7,052,496 B2 | 5/2006 | Yamauchi |
| 6,676,660 B2 | 1/2004 | Wampler et al. | | 7,063,715 B2 | 6/2006 | Onuki et al. |
| 6,676,676 B2 | 1/2004 | Danitz et al. | | D525,361 S | 7/2006 | Hushka |
| 6,679,882 B1 | 1/2004 | Kornerup | | 7,070,597 B2 | 7/2006 | Truckai et al. |
| 6,682,527 B2 | 1/2004 | Strul | | 7,083,618 B2 | 8/2006 | Couture et al. |
| 6,682,528 B2 | 1/2004 | Frazier et al. | | 7,083,619 B2 | 8/2006 | Truckai et al. |
| 6,685,724 B1 | 2/2004 | Haluck | | 7,083,620 B2 | 8/2006 | Jahns et al. |
| 6,689,131 B2 | 2/2004 | McClurken | | 7,087,051 B2 | 8/2006 | Bourne et al. |
| 6,692,445 B2 | 2/2004 | Roberts et al. | | 7,087,054 B2 | 8/2006 | Truckai et al. |
| 6,693,246 B1 | 2/2004 | Rudolph et al. | | 7,090,673 B2 | 8/2006 | Dycus et al. |
| 6,695,840 B2 | 2/2004 | Schulze | | 7,090,689 B2 | 8/2006 | Nagase et al. |
| 6,702,810 B2 | 3/2004 | McClurken et al. | | 7,101,371 B2 | 9/2006 | Dycus et al. |
| 6,723,092 B2 | 4/2004 | Brown et al. | | 7,101,372 B2 | 9/2006 | Dycus et al. |
| 6,726,068 B2 | 4/2004 | Miller | | 7,101,373 B2 | 9/2006 | Dycus et al. |
| 6,726,686 B2 | 4/2004 | Buysse et al. | | 7,103,947 B2 | 9/2006 | Sartor et al. |
| 6,726,694 B2 | 4/2004 | Blatter et al. | | 7,107,124 B2 | 9/2006 | Green |
| 6,733,498 B2 | 5/2004 | Paton et al. | | 7,112,199 B2 | 9/2006 | Cosmescu |
| 6,736,813 B2 | 5/2004 | Yamauchi et al. | | D531,311 S | 10/2006 | Guerra et al. |
| 6,743,229 B2 | 6/2004 | Buysse et al. | | 7,115,123 B2 | 10/2006 | Knowlton et al. |
| 6,743,230 B2 | 6/2004 | Lutze et al. | | 7,118,570 B2 | 10/2006 | Tetzlaff et al. |
| 6,743,239 B1 | 6/2004 | Kuehn et al. | | 7,118,587 B2 | 10/2006 | Dycus et al. |
| 6,743,240 B2 | 6/2004 | Smith et al. | | 7,131,860 B2 | 11/2006 | Sartor et al. |
| 6,755,843 B2 | 6/2004 | Chung et al. | | 7,131,970 B2 | 11/2006 | Moses et al. |
| 6,756,553 B1 | 6/2004 | Yamaguchi et al. | | 7,131,971 B2 | 11/2006 | Dycus et al. |
| 6,757,977 B2 | 7/2004 | Dambal et al. | | 7,135,020 B2 | 11/2006 | Lawes et al. |
| D493,888 S | 8/2004 | Reschke | | D533,942 S | 12/2006 | Kerr et al. |
| 6,770,072 B1 | 8/2004 | Truckai et al. | | 7,145,757 B2 | 12/2006 | Shea et al. |
| 6,773,409 B2 | 8/2004 | Truckai et al. | | 7,147,638 B2 | 12/2006 | Chapman et al. |
| 6,773,432 B1 | 8/2004 | Clayman et al. | | 7,150,097 B2 | 12/2006 | Sremcich et al. |
| 6,773,434 B2 | 8/2004 | Ciarrocca | | 7,150,749 B2 | 12/2006 | Dycus et al. |
| 6,773,441 B1 | 8/2004 | Laufer et al. | | 7,153,314 B2 | 12/2006 | Laufer et al. |
| 6,775,575 B2 | 8/2004 | Bommannan et al. | | D535,027 S | 1/2007 | James et al. |
| 6,776,780 B2 | 8/2004 | Mulier et al. | | 7,156,842 B2 | 1/2007 | Sartor et al. |
| 6,786,905 B2 | 9/2004 | Swanson et al. | | 7,156,846 B2 | 1/2007 | Dycus et al. |
| 6,790,217 B2 | 9/2004 | Schulze et al. | | 7,160,298 B2 | 1/2007 | Lawes et al. |
| 6,796,981 B2 | 9/2004 | Wham et al. | | 7,160,299 B2 | 1/2007 | Baily |
| D496,997 S | 10/2004 | Dycus et al. | | 7,169,146 B2 | 1/2007 | Truckai et al. |
| 6,800,825 B1 | 10/2004 | Sasaki et al. | | 7,179,255 B2 | 2/2007 | Lettice et al. |

| | | | |
|---|---|---|---|
| 7,179,258 B2 | 2/2007 | Buysse et al. | |
| 7,195,631 B2 | 3/2007 | Dumbauld | |
| D541,418 S | 4/2007 | Schechter et al. | |
| 7,207,990 B2 | 4/2007 | Lands et al. | |
| D541,938 S | 5/2007 | Kerr et al | |
| 7,223,264 B2 | 5/2007 | Daniel et al. | |
| 7,223,265 B2 | 5/2007 | Keppel | |
| 7,232,440 B2 | 6/2007 | Dumbauld et al. | |
| 7,241,288 B2 | 7/2007 | Braun | |
| 7,241,296 B2 | 7/2007 | Buysse et al. | |
| 7,244,257 B2 | 7/2007 | Podhajsky et al. | |
| 7,246,734 B2 | 7/2007 | Shelton, IV | |
| 7,248,944 B2 | 7/2007 | Green | |
| 7,252,667 B2 | 8/2007 | Moses et al. | |
| 7,255,697 B2 | 8/2007 | Dycus et al. | |
| 7,267,677 B2 | 9/2007 | Johnson et al. | |
| 7,270,660 B2 | 9/2007 | Ryan | |
| 7,270,664 B2 | 9/2007 | Johnson et al. | |
| 7,276,068 B2 | 10/2007 | Johnson et al. | |
| 7,300,435 B2 | 11/2007 | Wham et al. | |
| 7,303,557 B2 | 12/2007 | Wham et al. | |
| 7,311,709 B2 | 12/2007 | Truckai et al. | |
| 7,314,471 B2 | 1/2008 | Holman | |
| 7,318,823 B2 | 1/2008 | Sharps et al. | |
| 7,329,256 B2 | 2/2008 | Johnson et al. | |
| 7,329,257 B2 | 2/2008 | Kanehira et al. | |
| D564,662 S | 3/2008 | Moses et al. | |
| 7,338,526 B2 | 3/2008 | Steinberg | |
| 7,342,754 B2 | 3/2008 | Fitzgerald et al. | |
| 7,344,268 B2 | 3/2008 | Jhigamian | |
| D567,943 S | 4/2008 | Moses et al. | |
| 7,367,976 B2 | 5/2008 | Lawes et al. | |
| 7,377,920 B2 | 5/2008 | Buysse et al. | |
| 7,384,420 B2 | 6/2008 | Dycus et al. | |
| 7,384,421 B2 | 6/2008 | Hushka | |
| 7,396,336 B2 | 7/2008 | Orszulak et al. | |
| D575,395 S | 8/2008 | Hushka | |
| D575,401 S | 8/2008 | Hixson et al. | |
| 7,435,249 B2 | 10/2008 | Buysse et al. | |
| 7,442,193 B2 | 10/2008 | Shields et al. | |
| 7,442,194 B2 | 10/2008 | Dumbauld et al. | |
| 7,445,621 B2 | 11/2008 | Dumbauld et al. | |
| 7,458,972 B2 | 12/2008 | Keppel | |
| 7,473,253 B2 | 1/2009 | Dycus et al. | |
| 7,481,810 B2 | 1/2009 | Dumbauld et al. | |
| 7,487,780 B2 | 2/2009 | Hooven | |
| 7,491,201 B2 | 2/2009 | Shields et al. | |
| 7,491,202 B2 | 2/2009 | Odom et al. | |
| 7,500,975 B2 | 3/2009 | Cunningham et al. | |
| 7,510,556 B2 | 3/2009 | Nguyen et al. | |
| 7,513,898 B2 | 4/2009 | Johnson et al. | |
| 7,540,872 B2 | 6/2009 | Schechter et al. | |
| 7,549,995 B2 | 6/2009 | Schultz | |
| 7,553,312 B2 | 6/2009 | Tetzlaff et al. | |
| 7,799,026 B2 * | 9/2010 | Schechter et al. | 606/51 |
| 2002/0013583 A1 | 1/2002 | Camran et al. | |
| 2002/0049442 A1 | 4/2002 | Roberts et al. | |
| 2002/0099372 A1 | 7/2002 | Schulze et al. | |
| 2002/0107517 A1 | 8/2002 | Witt et al. | |
| 2002/0111624 A1 | 8/2002 | Witt et al. | |
| 2002/0188294 A1 | 12/2002 | Couture et al. | |
| 2003/0014052 A1 | 1/2003 | Buysse et al. | |
| 2003/0014053 A1 | 1/2003 | Nguyen et al. | |
| 2003/0018331 A1 | 1/2003 | Dycus et al. | |
| 2003/0018332 A1 | 1/2003 | Schmaltz et al. | |
| 2003/0032956 A1 | 2/2003 | Lands et al. | |
| 2003/0069570 A1 | 4/2003 | Witzel et al. | |
| 2003/0069571 A1 | 4/2003 | Treat et al. | |
| 2003/0078578 A1 | 4/2003 | Truckai et al. | |
| 2003/0109875 A1 | 6/2003 | Tetzlaff et al. | |
| 2003/0114851 A1 | 6/2003 | Truckai et al. | |
| 2003/0139741 A1 | 7/2003 | Goble et al. | |
| 2003/0139742 A1 | 7/2003 | Wampler et al. | |
| 2003/0158548 A1 | 8/2003 | Phan et al. | |
| 2003/0158549 A1 | 8/2003 | Swanson | |
| 2003/0171747 A1 | 9/2003 | Kanehira et al. | |
| 2003/0181910 A1 | 9/2003 | Dycus et al. | |
| 2003/0216732 A1 | 11/2003 | Truckai et al. | |
| 2003/0220637 A1 | 11/2003 | Truckai et al. | |
| 2003/0229344 A1 | 12/2003 | Dycus et al. | |
| 2003/0236325 A1 | 12/2003 | Bonora | |
| 2003/0236518 A1 | 12/2003 | Marchitto et al. | |
| 2004/0030330 A1 | 2/2004 | Brassell et al. | |
| 2004/0030332 A1 | 2/2004 | Knowlton et al. | |
| 2004/0039382 A1 * | 2/2004 | Kroll et al. | 606/41 |
| 2004/0049185 A1 | 3/2004 | Latterell et al. | |
| 2004/0064151 A1 | 4/2004 | Mollenauer | |
| 2004/0073238 A1 | 4/2004 | Makower | |
| 2004/0073256 A1 | 4/2004 | Marchitto et al. | |
| 2004/0078035 A1 | 4/2004 | Kanehira et al. | |
| 2004/0082952 A1 | 4/2004 | Dycus et al. | |
| 2004/0087943 A1 | 5/2004 | Dycus et al. | |
| 2004/0115296 A1 | 6/2004 | Duffin | |
| 2004/0116924 A1 | 6/2004 | Dycus et al. | |
| 2004/0116979 A1 * | 6/2004 | Truckai et al. | 607/51 |
| 2004/0143263 A1 | 7/2004 | Schechter et al. | |
| 2004/0148035 A1 | 7/2004 | Barrett et al. | |
| 2004/0162557 A1 | 8/2004 | Tetzlaff et al. | |
| 2004/0193153 A1 | 9/2004 | Sarter et al. | |
| 2004/0199181 A1 | 10/2004 | Knodel et al. | |
| 2004/0210282 A1 | 10/2004 | Flock et al. | |
| 2004/0224590 A1 | 11/2004 | Rawa et al. | |
| 2004/0230189 A1 | 11/2004 | Keppel | |
| 2004/0236326 A1 | 11/2004 | Schulze et al. | |
| 2004/0243125 A1 | 12/2004 | Dycus et al. | |
| 2004/0249374 A1 | 12/2004 | Tetzlaff et al. | |
| 2004/0260281 A1 | 12/2004 | Baxter, III et al. | |
| 2005/0004564 A1 | 1/2005 | Wham et al. | |
| 2005/0004569 A1 | 1/2005 | Witt et al. | |
| 2005/0033278 A1 | 2/2005 | McClurken et al. | |
| 2005/0059934 A1 | 3/2005 | Wenchell et al. | |
| 2005/0096645 A1 | 5/2005 | Wellman et al. | |
| 2005/0101951 A1 | 5/2005 | Wham et al. | |
| 2005/0101952 A1 | 5/2005 | Lands et al. | |
| 2005/0113818 A1 | 5/2005 | Sartor et al. | |
| 2005/0113819 A1 | 5/2005 | Wham et al. | |
| 2005/0113826 A1 | 5/2005 | Johnson et al. | |
| 2005/0149017 A1 | 7/2005 | Dycus | |
| 2005/0149151 A1 | 7/2005 | Orszulak et al. | |
| 2005/0154387 A1 | 7/2005 | Moses et al. | |
| 2005/0171535 A1 * | 8/2005 | Truckai et al. | 606/48 |
| 2005/0187547 A1 | 8/2005 | Sugi | |
| 2005/0197659 A1 | 9/2005 | Bahney | |
| 2005/0203504 A1 | 9/2005 | Wham et al. | |
| 2006/0052778 A1 | 3/2006 | Chapman et al. | |
| 2006/0052779 A1 | 3/2006 | Hammill | |
| 2006/0064085 A1 | 3/2006 | Schechter et al. | |
| 2006/0064086 A1 | 3/2006 | Odom | |
| 2006/0074417 A1 | 4/2006 | Cunningham et al. | |
| 2006/0079888 A1 | 4/2006 | Mulier et al. | |
| 2006/0079890 A1 | 4/2006 | Guerra | |
| 2006/0079891 A1 | 4/2006 | Arts et al. | |
| 2006/0079933 A1 | 4/2006 | Hushka et al. | |
| 2006/0084973 A1 | 4/2006 | Hushka | |
| 2006/0089670 A1 | 4/2006 | Hushka | |
| 2006/0116675 A1 | 6/2006 | McClurken et al. | |
| 2006/0129146 A1 | 6/2006 | Dycus et al. | |
| 2006/0167450 A1 | 7/2006 | Johnson et al. | |
| 2006/0167452 A1 | 7/2006 | Moses et al. | |
| 2006/0173452 A1 | 8/2006 | Buysse et al. | |
| 2006/0189981 A1 | 8/2006 | Dycus et al. | |
| 2006/0190035 A1 | 8/2006 | Hushka et al. | |
| 2006/0217709 A1 | 9/2006 | Couture et al. | |
| 2006/0229666 A1 | 10/2006 | Suzuki et al. | |
| 2006/0253126 A1 | 11/2006 | Bjerken et al. | |
| 2006/0259036 A1 | 11/2006 | Tetzlaff et al. | |
| 2006/0264922 A1 | 11/2006 | Sartor et al. | |
| 2006/0264931 A1 | 11/2006 | Chapman et al. | |
| 2006/0283093 A1 | 12/2006 | Petrovic et al. | |
| 2006/0287641 A1 | 12/2006 | Perlin | |
| 2007/0016182 A1 | 1/2007 | Lipson et al. | |
| 2007/0016187 A1 | 1/2007 | Weinberg et al. | |
| 2007/0043352 A1 | 2/2007 | Garrison et al. | |
| 2007/0043353 A1 | 2/2007 | Dycus et al. | |
| 2007/0060919 A1 | 3/2007 | Isaacson et al. | |
| 2007/0062017 A1 | 3/2007 | Dycus et al. | |
| 2007/0074807 A1 | 4/2007 | Guerra | |
| 2007/0078456 A1 | 4/2007 | Dumbauld et al. | |

| | | | | | |
|---|---|---|---|---|---|
| 2007/0078458 A1 | 4/2007 | Dumbauld et al. | DE | 19608716 | 4/1997 |
| 2007/0078459 A1 | 4/2007 | Johnson et al. | DE | 19751106 | 5/1998 |
| 2007/0088356 A1 | 4/2007 | Moses et al. | DE | 19751108 | 5/1999 |
| 2007/0106295 A1 | 5/2007 | Garrison et al. | DE | 19738457 | 1/2009 |
| 2007/0106297 A1 | 5/2007 | Dumbauld et al. | EP | 0364216 | 4/1990 |
| 2007/0118111 A1 | 5/2007 | Weinberg | EP | 0467501 | 1/1992 |
| 2007/0118115 A1 | 5/2007 | Artale et al. | EP | 0518230 | 12/1992 |
| 2007/0142833 A1 | 6/2007 | Dycus et al. | EP | 0541930 | 5/1993 |
| 2007/0142834 A1 | 6/2007 | Dumbauld | EP | 0572131 | 12/1993 |
| 2007/0156139 A1 | 7/2007 | Schechter et al. | EP | 0584787 | 3/1994 |
| 2007/0156140 A1 | 7/2007 | Baily | EP | 0589453 | 3/1994 |
| 2007/0173811 A1 | 7/2007 | Couture et al. | EP | 0589555 | 3/1994 |
| 2007/0173814 A1 | 7/2007 | Hixson et al. | EP | 0623316 | 11/1994 |
| 2007/0179499 A1 | 8/2007 | Garrison | EP | 0624348 | 11/1994 |
| 2007/0198011 A1 | 8/2007 | Sugita | EP | 0650701 | 5/1995 |
| 2007/0213712 A1 | 9/2007 | Buysse et al. | EP | 0694290 | 3/1996 |
| 2007/0255279 A1 | 11/2007 | Buysse et al. | EP | 0717966 | 6/1996 |
| 2007/0260235 A1 | 11/2007 | Podhajsky | EP | 0754437 | 3/1997 |
| 2007/0260238 A1 | 11/2007 | Guerra | EP | 0517243 | 9/1997 |
| 2007/0260241 A1 | 11/2007 | Dalla Betta et al. | EP | 0853922 | 7/1998 |
| 2007/0260242 A1 | 11/2007 | Dycus et al. | EP | 0875209 | 11/1998 |
| 2007/0265616 A1 | 11/2007 | Couture et al. | EP | 0878169 | 11/1998 |
| 2008/0004616 A1 | 1/2008 | Patrick | EP | 0887046 | 1/1999 |
| 2008/0009860 A1 | 1/2008 | Odom | EP | 0923907 | 6/1999 |
| 2008/0015575 A1 | 1/2008 | Odom et al. | EP | 0986990 | 3/2000 |
| 2008/0021450 A1 | 1/2008 | Couture | EP | 1034747 | 9/2000 |
| 2008/0033428 A1 | 2/2008 | Artale et al. | EP | 1034748 | 9/2000 |
| 2008/0039835 A1 | 2/2008 | Johnson et al. | EP | 1025807 | 10/2000 |
| 2008/0039836 A1 | 2/2008 | Odom et al. | EP | 1034746 | 10/2000 |
| 2008/0045947 A1 | 2/2008 | Johnson et al. | EP | 1050278 | 11/2000 |
| 2008/0058802 A1 | 3/2008 | Couture et al. | EP | 1053719 | 11/2000 |
| 2008/0082100 A1 | 4/2008 | Orton et al. | EP | 1053720 | 11/2000 |
| 2008/0091189 A1 | 4/2008 | Carlton | EP | 1055399 | 11/2000 |
| 2008/0114356 A1 | 5/2008 | Johnson et al. | EP | 1055400 | 11/2000 |
| 2008/0167651 A1 | 7/2008 | Tetzlaff et al. | EP | 1080694 | 3/2001 |
| 2008/0195093 A1 | 8/2008 | Couture et al. | EP | 1082944 | 3/2001 |
| 2008/0215051 A1 | 9/2008 | Buysse et al. | EP | 1159926 | 12/2001 |
| 2008/0243120 A1 | 10/2008 | Lawes et al. | EP | 1177771 | 2/2002 |
| 2008/0249527 A1 | 10/2008 | Couture | EP | 1301135 | 4/2003 |
| 2008/0312653 A1 | 12/2008 | Arts et al. | EP | 1330991 | 7/2003 |
| 2008/0319442 A1 | 12/2008 | Unger et al. | EP | 1486177 | 6/2004 |
| 2009/0012520 A1 | 1/2009 | Hixson et al. | EP | 1472984 | 11/2004 |
| 2009/0018535 A1 | 1/2009 | Schechter et al. | EP | 0774232 | 1/2005 |
| 2009/0024126 A1 | 1/2009 | Artale et al. | EP | 1527747 | 5/2005 |
| 2009/0043304 A1 | 2/2009 | Tetzlaff et al. | EP | 1530952 | 5/2005 |
| 2009/0048596 A1 | 2/2009 | Shields et al. | EP | 1532932 | 5/2005 |
| 2009/0062794 A1 | 3/2009 | Buysse et al. | EP | 1535581 | 6/2005 |
| 2009/0082766 A1 | 3/2009 | Unger et al. | EP | 1609430 | 12/2005 |
| 2009/0082767 A1 | 3/2009 | Unger et al. | EP | 1632192 | 3/2006 |
| 2009/0082769 A1 | 3/2009 | Unger et al. | EP | 1642543 | 4/2006 |
| 2009/0088738 A1 | 4/2009 | Guerra et al. | EP | 1645238 | 4/2006 |
| 2009/0088739 A1 | 4/2009 | Hushka et al. | EP | 1645240 | 4/2006 |
| 2009/0088740 A1 | 4/2009 | Guerra et al. | EP | 1649821 | 4/2006 |
| 2009/0088741 A1 | 4/2009 | Hushka et al. | EP | 1707143 | 10/2006 |
| 2009/0088744 A1 | 4/2009 | Townsend | EP | 1767163 | 3/2007 |
| 2009/0088745 A1 | 4/2009 | Hushka et al. | EP | 1769765 | 4/2007 |
| 2009/0088746 A1 | 4/2009 | Hushka et al. | EP | 1769766 | 4/2007 |
| 2009/0088747 A1 | 4/2009 | Hushka et al. | EP | 1929970 | 6/2008 |
| 2009/0088748 A1 | 4/2009 | Guerra et al. | EP | 1990019 | 11/2008 |
| 2009/0088749 A1 | 4/2009 | Hushka et al. | EP | 1683496 | 12/2008 |
| 2009/0088750 A1 | 4/2009 | Hushka et al. | GB | 623316 | 5/1949 |
| 2009/0112206 A1 | 4/2009 | Dumbauld et al. | GB | 1490585 | 11/1977 |
| 2009/0131934 A1 | 5/2009 | Odom et al. | GB | 2214430 A | 6/1989 |
| 2009/0149853 A1 | 6/2009 | Shields et al. | GB | 2213416 A | 8/1989 |
| 2009/0149854 A1 | 6/2009 | Cunningham et al. | JP | 61-501068 | 9/1984 |
| 2009/0171350 A1 | 7/2009 | Dycus et al. | JP | 65-502328 | 3/1992 |
| 2009/0171353 A1 | 7/2009 | Johnson et al. | JP | 5-5106 | 1/1993 |
| 2009/0182327 A1 | 7/2009 | Unger | JP | 5-40112 | 2/1993 |
| 2009/0187188 A1 | 7/2009 | Guerra et al. | JP | 06343644 A2 | 12/1994 |
| | | | JP | 07265328 A2 | 10/1995 |
| | FOREIGN PATENT DOCUMENTS | | JP | 08056955 A2 | 3/1996 |
| | | | JP | 08252263 A2 | 10/1996 |
| DE | 2514501 | 10/1976 | JP | 09010223 A2 | 1/1997 |
| DE | 2627679 | 1/1977 | JP | 11244298 A2 | 9/1999 |
| DE | 3612646 | 4/1987 | JP | 2000-342599 A2 | 12/2000 |
| DE | 8712328 | 3/1988 | JP | 2000-350732 A2 | 12/2000 |
| DE | 4303882 | 8/1994 | JP | 2001-008944 A2 | 1/2001 |
| DE | 4403252 | 8/1995 | JP | 2001-029356 A2 | 2/2001 |
| DE | 19515914 | 7/1996 | JP | 2001-128990 A2 | 5/2001 |
| DE | 29616210 | 1/1997 | | | |

| | | |
|---|---|---|
| SU | 401367 | 11/1974 |
| WO | WO 89/00757 | 1/1989 |
| WO | WO 92/04873 | 4/1992 |
| WO | WO 92/06642 | 4/1992 |
| WO | WO 93/21845 | 11/1993 |
| WO | WO 94/08524 | 4/1994 |
| WO | WO 94/20025 | 9/1994 |
| WO | WO 95/02369 | 1/1995 |
| WO | WO 95/07662 | 3/1995 |
| WO | WO 95/15124 | 6/1995 |
| WO | WO 96/05776 | 2/1996 |
| WO | WO 96/022056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/40861 | 8/1999 |
| WO | WO 99/51158 | 10/1999 |
| WO | WO 99/66850 | 12/1999 |
| WO | WO 00/24330 | 5/2000 |
| WO | WO 00/24331 | 5/2000 |
| WO | WO 00/36986 | 6/2000 |
| WO | WO 00/41638 | 7/2000 |
| WO | WO 00/47124 | 8/2000 |
| WO | WO 00/53112 | 9/2000 |
| WO | WO 01/17448 | 3/2001 |
| WO | WO 01/54604 | 8/2001 |
| WO | WO 02/07627 | 1/2002 |
| WO | WO 02/067798 | 9/2002 |
| WO | WO 02/080783 | 10/2002 |
| WO | WO 02/080784 | 10/2002 |
| WO | WO 02/080785 | 10/2002 |
| WO | WO 02/080786 | 10/2002 |
| WO | WO 02/080793 | 10/2002 |
| WO | WO 02/080794 | 10/2002 |
| WO | WO 02/080795 | 10/2002 |
| WO | WO 02/080796 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO 03/061500 | 7/2003 |
| WO | WO 03/090630 | 11/2003 |
| WO | WO 03/101311 | 12/2003 |
| WO | WO 2004/032776 | 4/2004 |
| WO | WO 2004/032777 | 4/2004 |
| WO | WO 2004/052221 | 6/2004 |
| WO | WO 2004/073488 | 9/2004 |
| WO | WO 2004/073490 | 9/2004 |
| WO | WO 2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 | 1/2005 |
| WO | WO 2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003.

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

Rothenberg et al. "Use of the LigaSure Vessel Sealing System in Minimally Invasive Surgery in Children" Int'l Pediatric Endosurgery Group (IPEG) 2000.

Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778 dated Oct. 31, 2000.
Int'l Search Report EP 98958575.7 dated Sep. 20, 2002.
Int'l Search Report EP 04013772 dated Apr. 1, 2005.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 04752343.6 dated Jul. 20, 2007.
Int'l Search Report EP 05013463.4 dated Sep. 28, 2005.
Int'l Search Report EP 05013895 dated Oct. 14, 2005.
Int'l Search Report EP 05016399 dated Jan. 5, 2006.
Int'l Search Report EP 05017281 dated Nov. 16, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021197.8 dated Jan. 31, 2006.
Int'l Search Report EP 05021779.3 dated Jan. 18, 2006.
Int'l Search Report EP 05021780.1 dated Feb. 9, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 06002279.5 dated Mar. 22, 2006.
Int'l Search Report EP 06005185.1 dated Apr. 18, 2006.
Int'l Search Report EP 06006716 dated Aug. 4, 2006.
Int'l Search Report EP 06008779.8 dated Jun. 13, 2006.
Int'l Search Report EP 06014461.5 dated Oct. 20, 2006.
Int'l Search Report EP 06020574.7 dated Sep. 21, 2007.
Int'l Search Report EP 06020583.8 dated Jan. 30, 2007.
Int'l Search Report EP 06020584.6 dated Jan. 12, 2007.
Int'l Search Report EP 06020756.0 dated Feb. 5, 2007.
Int'l Search Report EP 06 024122.1 dated Mar. 19, 2007.
Int'l Search Report EP 06024123.9 dated Feb. 26, 2007.
Int'l Search Report EP 07 001480.8 dated Apr. 12, 2007.
Int'l Search Report EP 07 001488.1 dated May 29, 2007.
Int'l Search Report EP 07 009026.1 dated Sep. 12, 2007.
Int'l Search Report Extended—EP 07 009029.5 dated Jul. 12, 2007.
Int'l Search Report EP 07 009321.6 dated Aug. 17, 2007.
Int'l Search Report EP 07 010672.9 dated Oct. 1, 2007.
Int'l Search Report EP 07 013779.9 dated Oct. 18, 2007.
Int'l Search Report EP 07 015191.5 dated Dec. 19, 2007.
Int'l Search Report EP 07 015601.3 dated Dec. 6, 2007.
Int'l Search Report EP 07 020283.3 dated Jan. 16, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report PCT/US98/18640 dated Dec. 17, 1998.
Int'l Search Report PCT/US98/23950 dated Dec. 29, 1998.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/US03/28534 dated Dec. 19, 2003.
Int'l Search Report PCT/US04/03436 dated Oct. 5, 2004.
Int'l Search Report PCT/US04/13273 dated Nov. 22, 2004.
Int'l Search Report PCT/US04/15311 dated Nov. 18, 2004.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report EP 09 152267.2 Dated Jun. 15, 2009.
Int'l Search Report EP 09 152898.4 Dated Jun. 10, 2009.
Int'l Search Report PCT/US09/032690 dated Jun. 16, 2009.
EP Search Report from EP Application No. EP 09 16 5753 dated Oct. 30, 2009.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.

* cited by examiner

VARIABLE RESISTOR JAW

BACKGROUND

1. Technical Field

The present disclosure relates to electrosurgical forceps for assuring uniform sealing of tissue when performing electrosurgical procedures. More particularly, the present disclosure relates to open, laparoscopic, or endoscopic bipolar electrosurgical forceps that includes reactive elements for driving different amounts of current through different parts of a jaw member of the forceps in order to achieve a more controlled distribution of energy along the length of the jaw.

2. Description of the Related Art

Forceps utilize mechanical action to constrict, grasp, dissect and/or clamp tissue. Electrosurgical forceps utilize both mechanical clamping action and electrical energy to effect hemostasis by heating the tissue and blood vessels. By controlling the intensity, frequency and duration of the electrosurgical energy applied through the jaw members to the tissue, the surgeon can coagulate, cauterize and/or seal tissue.

In order to effect a proper seal with larger vessels or thick tissue, many known instruments rely on control of mechanical parameters. Two predominant mechanical parameters that should be accurately controlled are the pressure applied to the tissue and the gap distance between the electrodes. As can be appreciated, both of these parameters are affected by the thickness of vessels or tissue. More particularly, accurate application of pressure is important for several reasons: to reduce the tissue impedance to a low enough value that allows enough electrosurgical energy through the tissue; to overcome the forces of expansion during tissue heating; and to contribute to the end tissue thickness, which is an indication of a good seal.

Even with control over mechanical parameters, however, the tissue portion nearest the pivot of the opposing jaw members tend to receive more energy delivery than the portions which are distal thereto. Resistance is expressed as resistivity multiplied by, the length divided by cross-sectional area. The resistance, thus, changes as the pressure of the jaws affects the thickness of material held therebetween and the jaw surface area changes. The increased pressure at the distal ends increases both electrical contact and decreases thickness of tissue, thereby requiring, in some instances, a greater amount of energy between the distal ends of the opposing jaw members in order to properly and effectively seal larger vessels or tissue. Relying on mechanical parameters alone, without taking into account energy dissipation along the length of the jaw, can lead to an ineffective seal. Energy distribution, if properly controlled, can assure a consistent and reliable tissue seal by compensating for changes in tissue impedance caused by changes in pressure, surface area, and thickness.

SUMMARY

A bipolar forceps for sealing tissue includes an end effector assembly having opposing first and second jaw members each having a proximal end and a distal end. The jaw members are movable relative to each other in order to grasp tissue therebetween. An electrically conductive surface having two or more conductive sealing plates and a dielectric layer is operably coupled to the first jaw member. Each sealing plate is connected to a reactive element and positioned along the electrically conductive surface from the proximal end to the distal end. The reactive element of the sealing plate positioned on the proximal end of the first jaw member has a different impedance than the reactive element positioned on the distal end. An electrically conductive surface having one or more conductive sealing plates is operably coupled to the second jaw member. Each electrically conductive surface on the jaw members is adapted to be connected to a source of electrosurgical energy such that the sealing plates are capable of conducting energy through tissue held therebetween to effect a tissue seal.

In embodiments, the reactive element is a capacitor, resistor, variable resistor, resistor series, capacitor series, and/or a variable resistor network. In embodiments, the dielectric layer is composed of shape memory materials. In embodiments, the bipolar forceps further includes a sensor for measuring one or more tissue properties. The sensor configures the reactive elements based on one or more tissue properties in order to effectively seal tissue. A feedback loop may be used for real time adjustment of the reactive elements.

The present disclosure also relates to a method of sealing tissue including the steps of: providing a bipolar forceps that includes first and second jaw members each having proximal and distal ends, the first jaw member having an electrically conductive surface having two or more conductive sealing plates and a dielectric disposed therebetween. Each sealing plate is connected to a reactive element and positioned along the electrically conductive surface from the proximal end to the distal end. The reactive element on the proximal end has a higher impedance than the reactive element on the distal end. An electrically conductive surface is included having one or more conductive sealing plates operably coupled to the second jaw member. The method also includes the steps of connecting the jaw members to a source of electrosurgical energy; actuating the jaw members to grasp tissue between opposing jaw members; conducting electrosurgical energy to the electrically conductive surfaces of the jaw members; and controlling the reactive elements of the first jaw member to regulate the electrosurgical energy along the jaw members to effect a tissue seal.

BRIEF DESCRIPTION OF THE DRAWINGS

Various embodiments of the present disclosure are described herein with reference to the drawings wherein.

DETAILED DESCRIPTION

Various embodiments of the present disclosure are described hereinbelow with reference to the accompanying drawings. Well-known functions or constructions are not described in detail to avoid obscuring the present disclosure in unnecessary detail. Those skilled in the art will understand that the present disclosure may be adapted for use with either a laparoscopic instrument, an endoscopic instrument or an open instrument; however, different electrical and mechanical connections and considerations may apply to each particular type of instrument. The novel aspects with respect to vessel and tissue sealing are generally consistent with respect to both the open, laparoscopic, and endoscopic designs. In the drawings and in the description that follows, the term "proximal", as is traditional, will refer to the end of the forceps that is closer to the user, while the term "distal" will refer to the end of the forceps that is further from the user.

Figure 1:
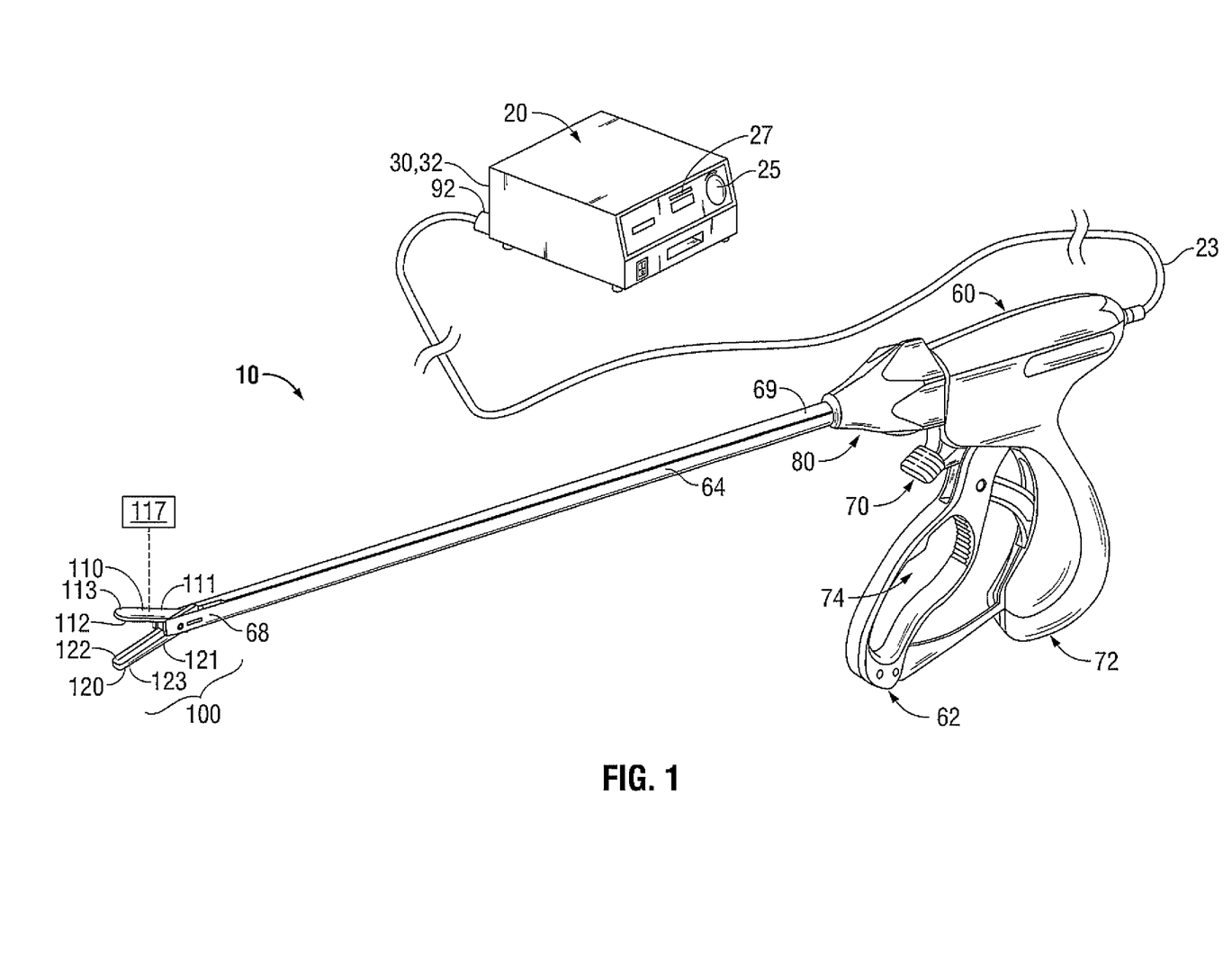
FIG. 1 is a perspective view of an electrosurgical system including an electrosurgical forceps and an electrical generator in accordance with an embodiment of the present disclosure.

Referring now to FIG. 1, a bipolar electrosurgical system according to the present disclosure is shown including electrosurgical forceps 10 configured to support end effector assembly 100. Forceps 10 typically includes various conventional features (e.g., a housing 60, a handle assembly 74, a rotating assembly 80, a trigger assembly 70, etc.) that enable forceps 10 and end effector assembly 100 to mutually cooperate to grasp, seal and, if warranted, divide tissue. Forceps 10 generally includes housing 60 and handle assembly 74 that includes moveable handle 62 and handle 72 which is integral with housing 60. Handle 62 is moveable relative to handle 72 to actuate end effector assembly 100 to grasp and treat tissue. Forceps 10 also includes shaft 64 that has distal end 68 that mechanically engages end effector assembly 100 and proximal end 69 that mechanically engages housing 60 proximate rotating assembly 80 disposed at the distal end of housing 60. Rotating assembly 80 is mechanically associated with shaft 64. Movement of rotating assembly 80 imparts similar rotational movement to shaft 64 which, in turn, rotates end effector assembly 100.

End effector assembly 100 includes two jaw members 110 and 120 having proximal ends 111, 121 and distal ends 113, 123. Jaw members 110 and 120 are movable from a first position wherein jaw members 110 and 120 are spaced relative to another, to a second position wherein jaw members 110 and 120 are closed and cooperate to grasp tissue therebetween. Each jaw member 110 and 120 includes electrically conductive surface 112 and 122, respectively, disposed on an inner-facing surface thereof. Electrically conductive surfaces 112 and 122 cooperate to seal tissue held therebetween upon the application of electrosurgical energy. Electrically conductive surfaces 112 and 122 are connected to generator 20 that communicates electrosurgical energy through the tissue held therebetween. A dielectric layer, or insulator substance, 114 may be included to limit and/or reduce many of the known undesirable effects related to tissue sealing, e.g., flashover, thermal spread and stray current dissipation. By controlling the intensity, frequency and duration of the electrosurgical energy applied to tissue, the tissue can be selectively sealed.

Generator 20 includes a plurality of outputs for interfacing with various electrosurgical instruments (e.g., a monopolar active electrode, return electrode, bipolar electrosurgical forceps, footswitch, etc.). Further, generator 20 includes suitable electronic circuitry configured for generating radio frequency power specifically suited for sealing tissue.

Forceps 10 are connected to a source of electrosurgical energy, e.g., electrosurgical generator 20, via one or more electrical cables. Electrically conductive surfaces 112 and 122, that act as active and return electrodes, are connected to the generator 20 through cable 23, which includes the supply and return lines coupled to active and return terminals 30, 32. Electrosurgical forceps 10 is coupled to generator 20 at active and return terminals 30 and 32 (e.g., pins) via plug 92 disposed at the end of cable 23, wherein plug 92 includes contacts from the supply and return lines. Electrosurgical RF energy is supplied to forceps 10 by generator 20 via a supply line connected to the active electrode and returned through a return line connected to the return electrode.

Generator 20 includes suitable input controls 25 (e.g., buttons, activators, switches, touch screen, etc.) for controlling the generator 20. In addition, generator 20 includes one or more display screens 27 for providing the surgeon with variety of output information (e.g., intensity settings, treatment complete indicators, etc.). The controls allow the surgeon to adjust power of the RF energy, waveform, and other suitable parameters to achieve the desired waveform suitable for a particular task (e.g., coagulating, tissue sealing, division with hemostatis, etc.). Further, forceps 10 may include a plurality of input controls that may be redundant with certain input controls 25 of generator 20. Placing the input controls at forceps 10 allows for easier and faster modification of RF energy parameters during the surgical procedure without requiring interaction with generator 20.

When the electrosurgical energy is transferred to the end effector assembly 100, a sensor, schematically illustrated as 117, may be employed to determine pre-surgical, concurrent surgical (i.e., during surgery), and/or post-surgical conditions. The sensor 117 may be any of a variety of sensors, such as, for example, a thickness sensor, optical sensor, or proximal sensor. The sensor 117 may measure tissue properties such as tissue thickness, tissue hydration level, tissue impedance, tissue density, tissue type, and other tissue properties as within the purview of those skilled in the art. The sensor 117 may also measure standard electrical parameters such as voltage, current, impedance, and phase. The sensor may be utilized with a closed-loop feedback system coupled to the electrosurgical generator to regulate the electrosurgical energy based upon one or more pre-surgical, concurrent surgical, or post surgical conditions. The feedback loop provides real-time adjustment of the reactive elements based on the tissue property being measured. It is also contemplated that forceps 10 and/or electrosurgical generator 20 used in connection with forceps 10 may include a sensor or feedback mechanism which automatically selects the appropriate amount of electrosurgical energy to effectively seal the particularly-sized tissue grasped between jaw members 110 and 120. The sensor or feedback mechanism may also measure the impedance across the tissue during sealing and provide an indicator (visual and/or audible) that an effective seal has been created between jaw members 110 and 120. Various sensor mechanisms and feedback systems are described in commonly-owned, co-pending U.S. patent application Ser. No. 10/427,832 entitled "METHOD AND SYSTEM FOR CONTROLLING OUTPUT OF RF MEDICAL GENERATOR" filed on May 1, 2003.

Other electrical connections are positioned through shaft 64 and end effector assembly 100 to supply bipolar electrical energy to opposing electrically conductive surfaces 112 and 122 of jaw members 110 and 120, respectively. Forceps 10 also includes a drive assembly (not explicitly shown) that imparts movement of jaw members 110 and 120 from the open position to the clamping or closed position. When electrically conductive surfaces 112 and 122 of jaw members 110 and 120 are fully compressed about the tissue, forceps 10 is ready for selective application of electrosurgical energy.

The details relating to the inter-cooperative relationships of the inner-working components of forceps 10 are disclosed in commonly-owned U.S. patent application Ser. No. 11/348,072. Mechanical and cooperative relationships with respect to the various moving elements of handle assembly 741 rotating assembly 80, and end effector assembly 100 are further described by example with respect to commonly-owned U.S. patent application Ser. Nos. 10/369,894 and 10/460,926.

Figure 2A:
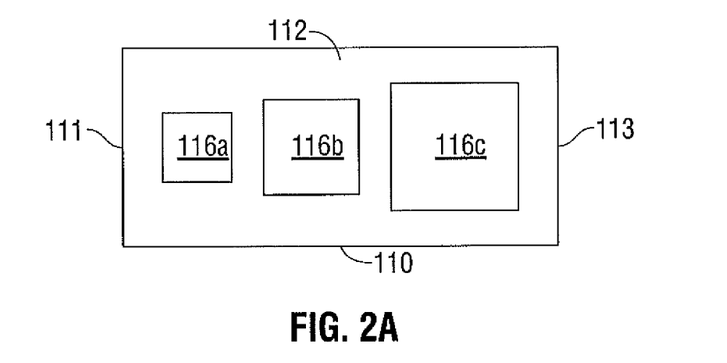
FIG. 2A is a plan view of the electrically conductive surface of a jaw member in accordance with the present disclosure.

Referring now to FIG. 2A, a plan view of electrically conductive surface 112 of jaw member 110 is shown. First jaw member 110 includes one or more sealing plates 116 on electrically conductive surface 112. Sealing plates 116a, 116b, and 116c are positioned along electrically conducting surface 112 from proximal end 111 to distal end 113. Sealing plates 116a, 116b, and 116c each include at least one reactive element for effecting a tissue seal. Reactive elements may include a capacitor, resistor, variable resistor, resistor series, capacitor series, and/or variable resistor network, as will be described in detail below.

Figure 2B:
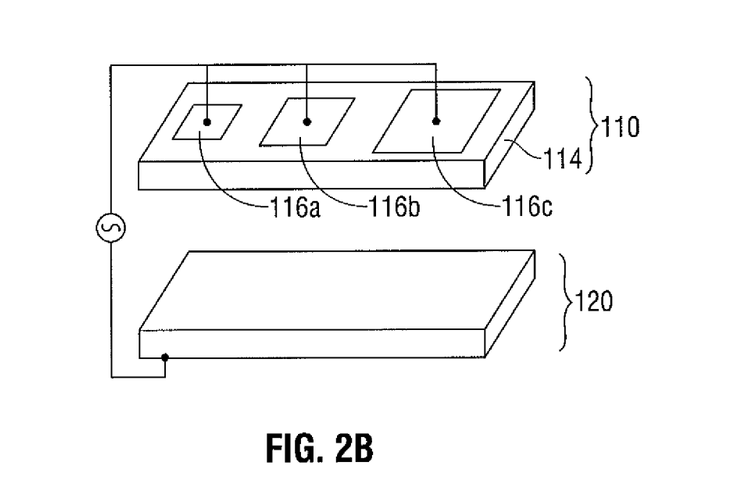
FIG. 2B is a perspective view of an embodiment of the jaw members in accordance with the present disclosure.
Figure 2C:
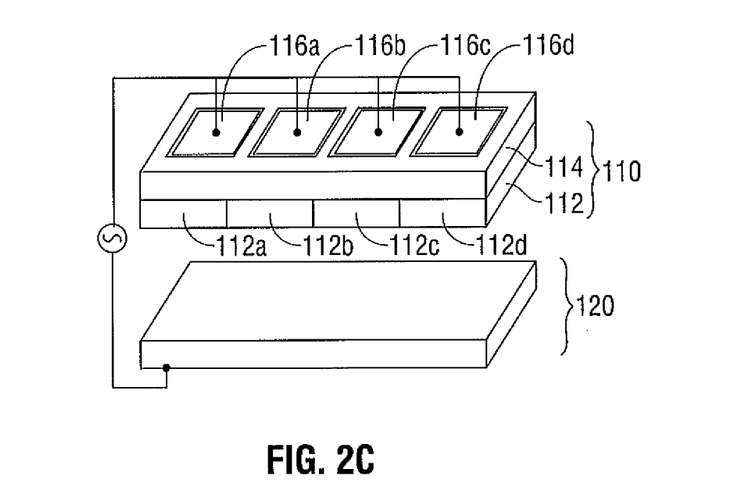
FIG. 2C is a perspective view of another embodiment of the jaw members in accordance with the present disclosure.
Figure 2D:
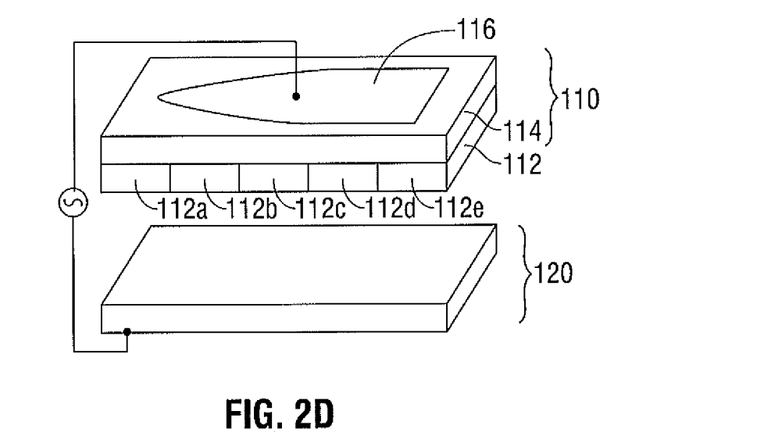
FIG. 2D is a perspective view of yet another embodiment of the jaw members in accordance with the present disclosure.

As illustrated in FIGS. 2B-2D, different embodiments are envisioned for altering the impedance at different locations about first jaw member 110. As shown in FIG. 2B, first jaw member 110 includes sealing plates 116a, 116b, and 116c disposed about dielectric 114. FIG. 2C illustrates first jaw member 110 including sealing plates 116a, 116b, 116c, and 116d placed proximal to dielectric 114, which is proximal to electrically conductive sealing surface 112, which is composed of electrically isolated sections 112a, 112b, 112c, and 112d having substantially the same geometry as the sealing plates. FIG. 2D illustrates seal plate 116 having a variable width along the length of jaw member 110 that is proximal to dielectric 114. Single sealing plate 116 provides a smooth change in capacitance along the length of the jaw. Slotted electrically conductive surface 112 allows each electrically isolated section 112a, 112b, 112c, 112d, and 112e to couple to sealing plate 116 independently and spread current.

Figure 2E:
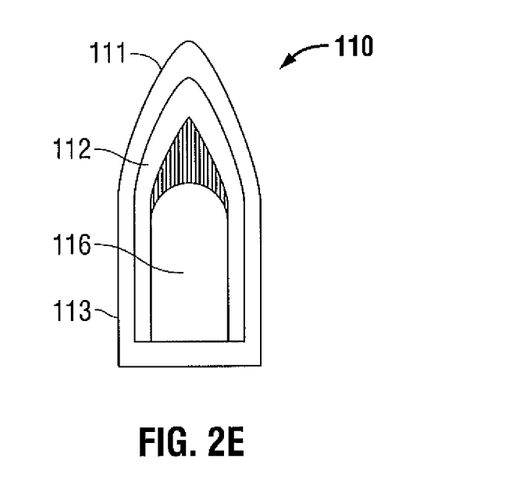
FIG. 2E is a plan view of another embodiment of the electrically conductive surface of a jaw member in accordance with the present disclosure.

Sealing plates 116 may be arranged in any configuration conducive to effectively seal tissue as understood by those skilled in the art. Further, the jaw member may have any suitable number of seal plates in any suitable design, such as the jaw member illustrated in FIG. 2E. Sealing plates 116 may be composed of metal, such as surgical stainless steel, or other conducting materials, such as, for example, carbon. Non-conducting material 114 may be an insulating material, such as, for example, polymers including, but not limited to, polyethylene, polytetrafluoroethylene, ethylene propylene diene monomer rubber, and the like. In a like manner, second jaw member 120 may also have a similar construction as jaw member 110 described above and include one or more sealing plates.

Figure 2F:
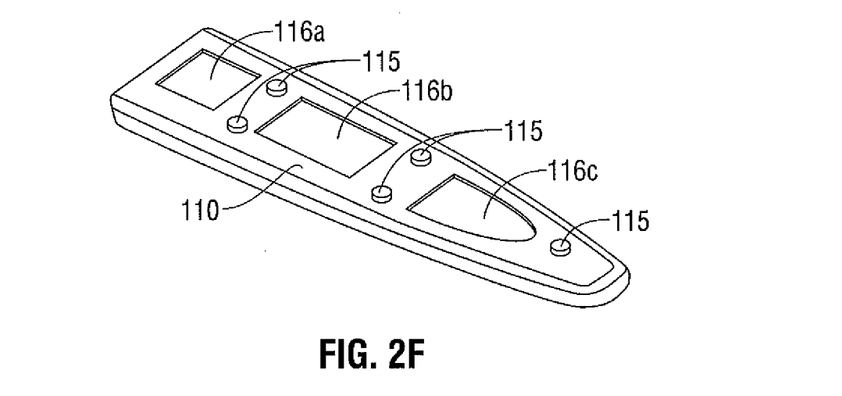
FIG. 2F is a perspective view of one embodiment of the electrically conductive surface of a jaw member including stop members in accordance with the present disclosure.

In some embodiments, at least one stop member 115, as illustrated in FIG. 2F, may be disposed on the inner facing surfaces of electrically conductive sealing surface 112 or 122 to facilitate gripping and manipulation of tissue and to define a gap between opposing jaw members 110 and 120 during sealing and/or cutting of tissue. Stop member 115 may extend from the sealing surface 122 a predetermined distance according to the specific material properties (e.g., compressive strength, thermal expansion, etc.) to yield a consistent and accurate gap distance during sealing. In embodiments, the gap distance between opposing sealing surfaces 112 and 122 during sealing ranges from about 0.001 inches to about 0.006 inches or, in other embodiments, from about 0.002 and about 0.003 inches. The non-conductive stop members 115 may be part of dielectric layer 114. Stop member 115 may also be molded onto jaw members 110 and 120 (e.g., over-molding, injection molding, etc.), stamped onto the jaw members 110 and 120, or deposited (e.g., deposition) onto the jaw members 110 and 120, such as by thermal spraying.

Figure 3:
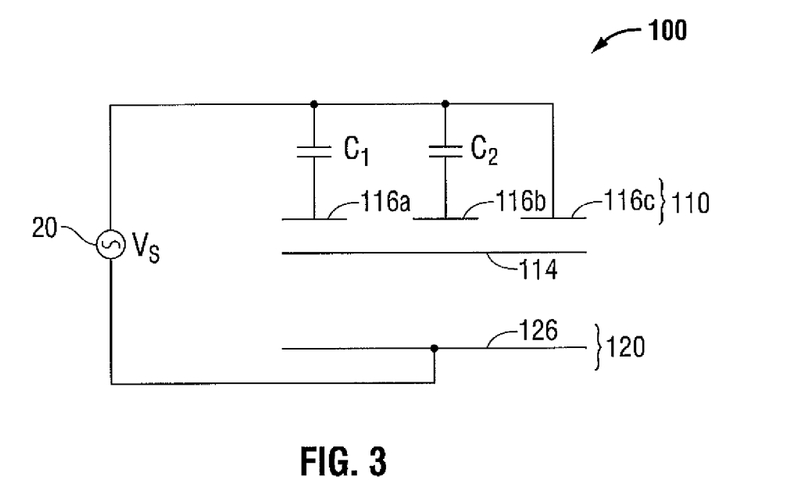
FIG. 3 is a schematic electrical diagram of the end effector assembly and generator of the electrosurgical forceps of FIG. 1.

FIG. 3 illustrates a schematic diagram of end effector assembly 100 and generator 20 according to an embodiment of the disclosure. Generator 20 provides a source voltage, $V_S$, to jaw members 110 and 120, Disposed between conductive sealing plates 116 and 126 of jaw members 110 and 120 is a dielectric, or non-conducting layer, 114, thereby forming a capacitor when compressed on tissue having a capacitance between each of the sealing plates 116 (e.g., $C_1$ and $C_2$).

Figure 2G:
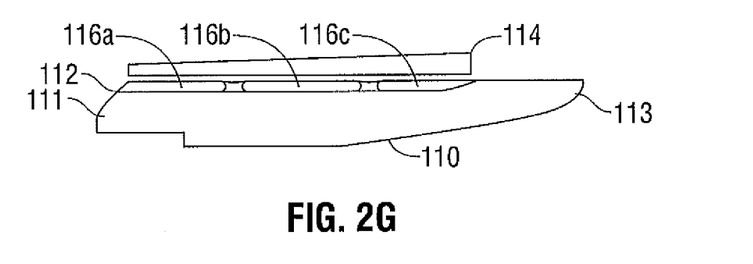
FIG. 2G is a side view of one embodiment of the electrically conductive surface of a jaw member including a dielectric layer of varying width in accordance with the present disclosure.

The width and thickness of dielectric layer 114 and the surface area of plates 116a, 116b, and 116c may be adjusted to achieve specific capacitances, which represent a specific impedance to RF generator 20. Dielectric layer 114 may have a varying thickness across the surface thereof, such that, for example, dielectric layer 114 is of one thickness around plate 116a, another thickness around plate 116b, and yet another thickness around plate 116c, as illustrated in FIG. 2G. In some embodiments, the dielectric layer 114 may be of varying thickness or material composition across conducting surface 112 or each plate 116, e.g. the carbon amount in filled ethylene propylene diene monomer rubber (EPDM) may be varied along the length of jaw members 110 and 120.

Capacitance and area are calculated based on standard capacitance formula:

$$C(E_R, A, d) = \frac{E_O \cdot E_R \cdot A}{d}$$

$$A_C(C, E_R, d) = \frac{C \cdot d}{E_O \cdot E_R}$$

wherein: $E_O$ is the absolute permittivity=$8.854*10^{-12}$ Farad/meter (F/m), $E_R$ is the relative permittivity of the insulation material in (F/m), A is the surface area of the jaws in meters squared (m²), and d is the distance between the jaws in meters (m).

The relative permittivity, $E_R$, varies with substance or material selection, examples of which are given in Table 1:

TABLE 1

| Material | Relative Permittivity (F/m) |
|---|---|
| Air | 1.0 |

TABLE 1-continued

| Material | Relative Permittivity (F/m) |
|---|---|
| Polythene/Polyethylene | 2.3 |
| PTFE | 2.1 |
| Silicone Rubber | 3.1 |
| FR4 Fiberglass | 4.5 |
| PVC | 5.0 |

The formula to calculate the impedance of a capacitor at the specified frequency C in hertz, is in Farads F:

$$R_C(C, F) = \frac{1}{2 \cdot \pi \cdot F \cdot C}$$

$$C_R(R, F) = \frac{1}{2 \cdot \pi \cdot F \cdot R}$$

For example, assuming that capacitances, $C_1$=500 ohms and $C_2$=1000 ohms, are desired at 472 Khz, and a high dielectric with a relative permittivity of 5.0 ($E_R$=5.0) and a thickness of 0.5 mm is used. The sealing plate areas needed are calculated as follow:

$E_R$=5.0 $d$=0.5×10$^{-3}$ $r$=500 $f$=470×10$^{-3}$ $A_C(Cr,f),E_R,d$)=7.649×10$^{-3}$m $E_R$=5.0 $d$=0.5×10$^{-3}$ $r$=500 $f$=470×10$^{-3}$ $A_C(Cr,f),E_R,d$)=3.825×10$^{-3}$m

Taking the square root of the area derived, to create a capacitor of equivalent impedance of 500 ohms at 472 Khz, a sealing plate of 2.77 mm$^2$ is required. For the 1000 ohm impedance, a sealing plate of 2 mm$^2$ would be used.

Figure 4:
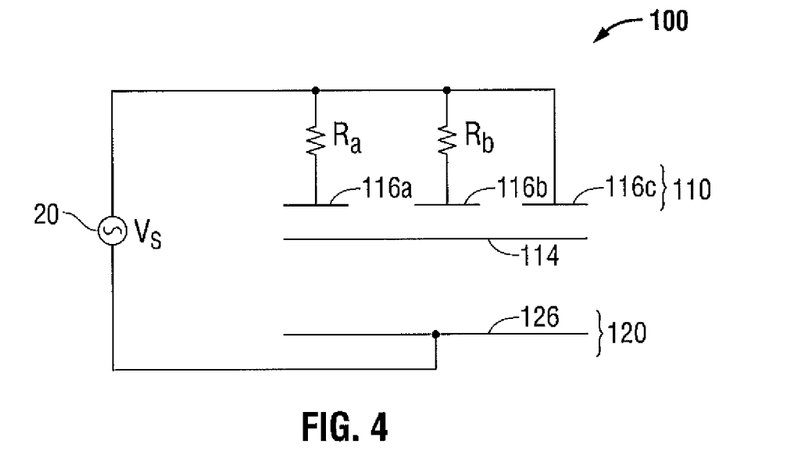
FIG. 4 is a schematic electrical diagram of another embodiment of the end effector assembly and generator in accordance with the present disclosure.

By specifically designing the sealing plates 116 and dielectric layer 114 to have a certain capacitive impedance, the circuit of FIG. 4 can be established. Generator 20 generates a source voltage, $V_S$. First jaw 110 includes three sealing plates 116a, 116b, and 116c separated from sealing plate 126 of second jaw member 120 via dielectric 114. Source voltage $V_S$ is constant and is applied across all three sealing plates 116a, 116b, and 116c. Sealing plates 116a and 116b, however, include parallel reactive elements $R_a$ and $R_b$, respectively $R_a$ has a greater resistance than $R_b$ such that with application of a constant voltage, the impedance to the tissue through sealing plates 116a, 116b, and 116c increase towards the proximal end of law members 110 and 120, thereby driving more current through distal end 111. In FIG. 4, and other embodiments described herein, the reactive elements, R, may be any of capacitors, resistors, variable resistors, resistor series, capacitor series, and/or variable resistor networks to provide the impedance needed to control current through the jaws and is therefore not limited to the particular reactive element exemplified in the embodiments.

Figure 5:
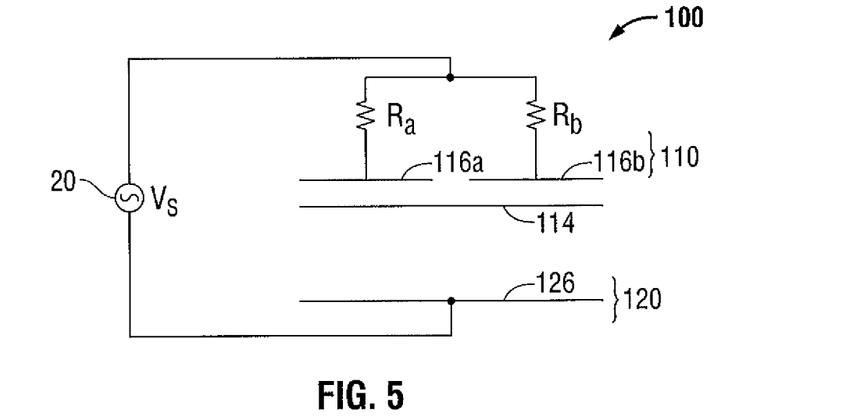
FIG. 5 is a schematic electrical diagram of another embodiment of the end effector assembly and generator in accordance with the present disclosure.

End effector assembly 100 may be constructed as shown, or in reverse, so that jaw member 120 includes more than one plate and associated reactive element. In some embodiments, such as that shown in FIG. 5, jaw member 110 can be split into proximal and distal sealing plates, 116a and 116b, connected by the same wire from voltage source, $V_S$, but with increased impedance between the wire and the proximal end by use of reactive element $R_a$ which is greater than $R_b$.

Figure 6:
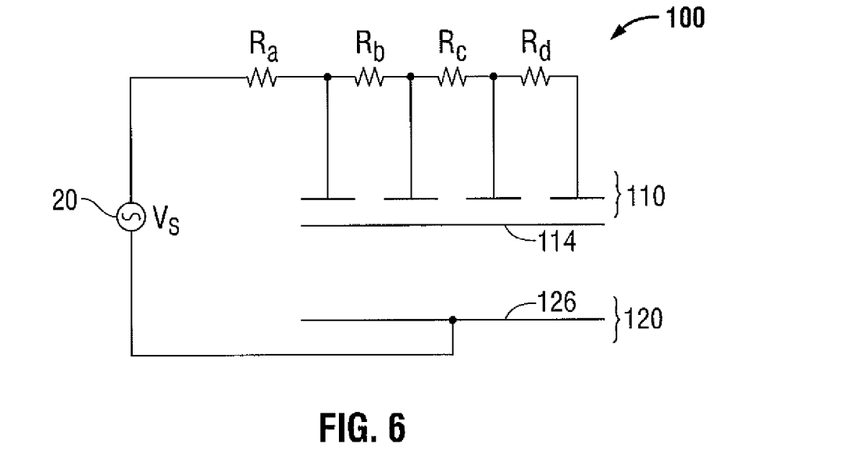
FIG. 6 is a schematic electrical diagram of another embodiment of the end effector assembly and generator with the resistors arranged in series in accordance with the present disclosure.

In yet other embodiments, such as that shown in FIG. 6, resistors $R_a$, $R_b$, $R_c$, and $R_d$ are connected in series across voltage source $V_S$, thereby forming a voltage divider. The voltage divider may consist of any two or more resistors connected in series across voltage source 20. Resistors $R_a$, $R_b$, $R_c$, and $R_d$ decrease in resistance along the length of jaw member 110 towards distal end 113. The source voltage $V_S$ must be as high as or higher than any voltage developed by the voltage divider. As the source voltage is dropped in successive steps through the series resistors, the source voltage is tapped off to supply individual voltage requirements to each sealing plate 116. The values of the series resistors used are determined by the voltage and current requirements of sealing plates 116a, 116b, and 116c as explained above.

Figure 7:
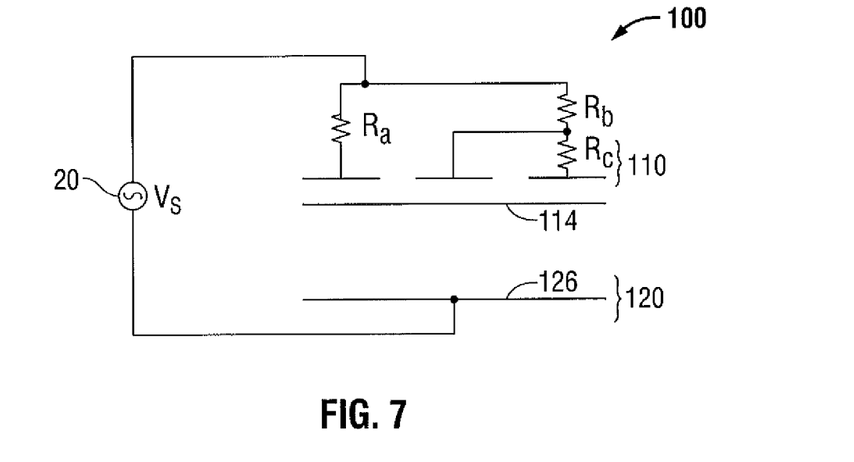
FIG. 7 is a schematic electrical diagram of another embodiment of the end effector assembly and generator of the electrosurgical forceps.

In other embodiments, any number of suitable sealing plates may be used with any suitable number of resistors in any of the configurations described above, such as, for example, as illustrated in FIG. 7.

Figure 8:
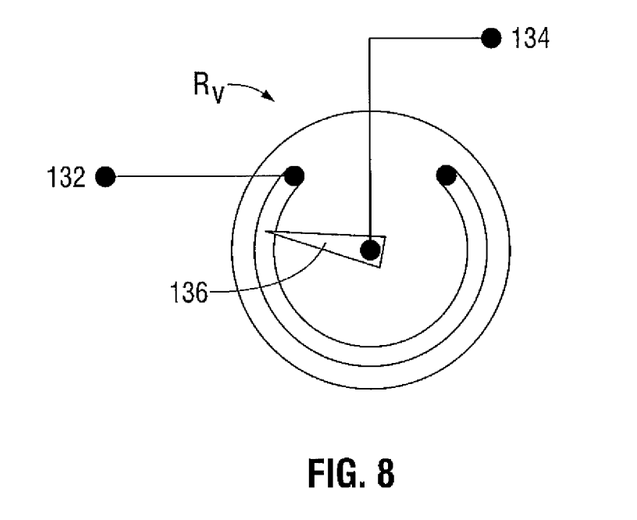
FIG. 8 is a schematic electrical diagram of a variable resistor which may be used with the electrosurgical forceps in accordance with the present disclosure.

In other embodiments, variable resistors may be used. Variable resistor, $R_v$, such as that shown in FIG. 8, allows adjustment of the resistance between two points, 132 and 134, in the circuit via spindle 136. It is useful for setting the value of the resistor while in use depending on changes in other parameters, such as, for example, the distance between plates 116, 126.

It is also envisioned that the dielectric 114 may be made of a material that expands with temperature, such as shape memory alloys or polymers. Shape memory alloys (SMAs) are a family of alloys having anthropomorphic qualities of memory and trainability and are particularly well suited for use with medical instruments. One of the most common SMAs is Nitinol which can retain shape memories for two different physical configurations and changes shape as a function of temperature. Recently, other SMAs have been developed based on copper, zinc and aluminum and have similar shape memory retaining features.

SMAs undergo a crystalline phase transition upon applied temperature and/or stress variations. A particularly useful attribute of SMAs is that after it is deformed by temperature/stress, it can completely recover its original shape on being returned to the original temperature. The ability of an alloy to possess shape memory is a result of the fact that the alloy undergoes a reversible transformation from an austenite state to a martensite state with a change in temperature (or stress-induced condition). This transformation is referred to as a thermoelastic martensite transformation.

Under normal conditions, the thermoelastic martensite transformation occurs over a temperature range that varies with the composition of the alloy, itself, and the type of thermal-mechanical processing by which it was manufactured. In other words, the temperature at which a shape is "memorized" by an SMA is a function of the temperature at which the martensite and austenite crystals form in that particular alloy. For example, Nitinol alloys can be fabricated so that the shape memory effect will occur over a wide range of temperatures, e.g., −270° to +100° Celsius.

Shape memory polymers (SMPs) may be used instead of, or may augment the use of, SMAs. SMPs are generally characterized as phase segregated linear block co-polymers having a hard segment and a soft segment. The hard segment is typically crystalline, with a defined melting point, and the soft segment is typically amorphous, with a defined glass transition temperature. In embodiments, however, the hard segment may be amorphous and have a glass transition temperature and the soft segment may be crystalline and have a melting point. The melting point or glass transition temperature of the soft segment is substantially less than the melting point or glass transition temperature of the hard segment.

When the SMP is heated above the melting point of the hard segment the material can be shaped. This shape can be memorized by cooling the SMP below the melting point of the hard segment. When the shaped SMP is cooled below the glass transition temperature of the soft segment while the shape is deformed, a new temporary shape can be set. The original shape can be recovered by heating the material above the glass transition temperature of the soft segment but below the melting point of the hard segment. The recovery of the original shape, which is induced by an increase in temperature, is called the thermal shape memory effect.

Because capacitance is proportional to the dielectric constant and to the surface area of the plates and inversely proportional to the distance between the plates, a dielectric composed of shape memory material that expands with temperature will result in decreased capacitance and increased jaw impedance. Thus, a jaw constructed of shape memory materials will impede RF as the temperature rises.

Figure 9:
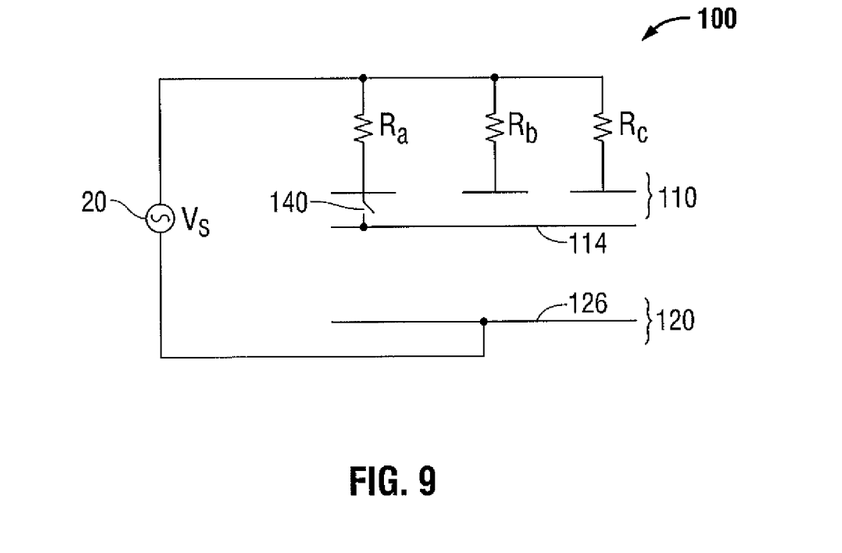
FIG. 9 is a schematic electrical diagram of an end effector assembly and generator having a shape memory switch.

It is also envisioned, as illustrated in FIG. 9, that a switch may be utilized with the embodiments of the present disclosure. Switch 140 may be composed of a shape memory material to detect a change in temperature of current. Switch 140 establishes contact with a corresponding electrical contact when a particular temperature is reached to allow current to flow therethrough.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto

What is claimed is:

1. A bipolar forceps for sealing tissue, comprising:
    an end effector assembly having opposing first and second jaw members each having a proximal end and a distal end and being movable relative to one another to grasp tissue therebetween;
    a first electrically conductive surface having at least two conductive sealing plates and a dielectric layer operably coupled to the first jaw member and forming an inner-facing surface thereof, each of the at least two conductive sealing plates connected to at least one reactive element, the at least two conductive sealing plates including a first sealing plate and a second sealing plate, the first sealing plate being positioned along the first electrically conductive surface proximal to the second sealing plate, the at least one reactive element connected to the first sealing plate having a different impedance than the at least one reactive element connected to the second sealing plate; and
    a second electrically conductive surface having at least one conductive sealing plate operably coupled to the second jaw member and forming an inner-facing surface thereof,
    wherein each of the first and second electrically conductive surfaces is adapted to connect to a source of electrosurgical energy,
    wherein a first impedance to tissue is formed by the reactive element of the first sealing plate and a second impedance to tissue is formed by the reactive element of the second sealing plate, wherein the first impedance is greater than the second impedance thereby driving more current through the distal end of the first electrically conductive surface, such that the first and second electrically conductive surfaces are capable of conducting energy through tissue held therebetween to effect a tissue seal.

2. The bipolar forceps of claim 1 wherein the at least one reactive element is at least one of a capacitor, resistor, variable resistor, resistor series, capacitor series, and variable resistor network.

3. The bipolar forceps of claim 1 wherein the dielectric layer is disposed between adjacent sealing plates along a length of the first jaw member.

4. The bipolar forceps of claim 3, wherein the dielectric layer separates and electrically isolates adjacent sealing plates along the length of the first jaw member.

5. The bipolar forceps of claim 1 wherein the dielectric layer varies in thickness along, the length of the jaw member.

6. The bipolar forceps of claim 1 wherein the dielectric layer is composed of a shape memory material.

7. The bipolar forceps of claim 1 wherein the dielectric layer acts as a stop member to regulate distance between jaw members.

8. The bipolar forceps of claim 1 wherein the electrically conductive surfaces have stop members.

9. The bipolar forceps of claim 1 further comprising:
    a sensor which measures at least one tissue property and configures the at least one reactive element based on the at least one tissue property to effectively seal tissue.

10. The bipolar forceps of claim 9 wherein the at least one tissue property measured by the sensor includes at least one of tissue thickness, tissue hydration level, tissue impedance, tissue density, tissue type, voltage, current, impedance, and phase.

11. The bipolar forceps of claim 9 further comprising a feedback loop for real time adjustment of the at least one reactive element based on the at least one tissue property.

12. The bipolar forceps of claim 9 wherein the at least one reactive element is at least one of a capacitor, resistor, variable resistor, resistor series, capacitor series, and variable resistor network.

13. The bipolar forceps of claim 1, wherein the first sealing plate of the first electrically conductive surface has a different surface area than the second sealing plate of the first electrically conductive surface.

* * * * *